(12) United States Patent
Jones et al.

(10) Patent No.: US 6,945,096 B1
(45) Date of Patent: *Sep. 20, 2005

(54) MEASUREMENT AND CONTROL OF ASPHALTENE AGGLOMERATION IN HYDROCARBON LIQUIDS

(75) Inventors: Gregory M. Jones, Formby (GB); Malcolm J. W. Povey, Huddersfield (GB); John Campbell, Liverpool (GB)

(73) Assignees: Baker Hughes Incorporated, Houston, TX (US); The University of Leeds, Leeds (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/509,126
(22) PCT Filed: Oct. 8, 1998
(86) PCT No.: PCT/US98/21287
§ 371 (c)(1), (2), (4) Date: Mar. 22, 2000
(87) PCT Pub. No.: WO99/19723
PCT Pub. Date: Apr. 22, 1999

Related U.S. Application Data (63) Continuation-in-part of application No. 08/947,821, filed on Oct. 9, 1997, now Pat. No. 5,969,237.

(51) Int. Cl.[7] .............................................. G01N 29/02
(52) U.S. Cl. ..................... 73/61.75; 73/64.42
(58) Field of Search ............................. 73/61.75, 61.71, 73/64.41, 64.42, 64.53, 53.05, 602, 599, 610, 629, 865.5, 611

(56) References Cited

U.S. PATENT DOCUMENTS

| 4,706,509 A | * | 11/1987 | Riebel | 73/53.05 |
| 5,132,225 A | * | 7/1992 | Dickakian | 73/53.05 |
| 5,420,040 A | * | 5/1995 | Anfindsen et al. | 73/53.05 |
| 5,853,994 A | * | 12/1998 | Gopinathan et al. | 73/61.75 |

OTHER PUBLICATIONS

Holmes et al. J. Coll. Interfac. Sci. vol. 156 (1993) 261–268.*
Dickinson et al. J. Coll. Interfac. Sci. vol. 142 (Mar. 1991) 103–110.*
McClements et al. J. Coll Interfac. Sci. vol. 160 (1993) 293–297.*
McClements et al. Ultrasonics vol. 31 (1993) 433–437.*
McClements et al. J. Phys. D: Appl. Phys. vol. 22 (1989) 38–47.*
Pinfield et al. J. Phys. Chem B vol. 101 (1997) 1110–1112.*
Pinfield et al. Ultrasonics vol. 33 (1995) 243–251.*
Pinfield et al. J. Coll Interfac. Sci. vol. 166 (1994) 363–374.*
Behrman et al. MBAA Technical Quarterly vol. 24 (1987) 72–76.*
Bouts et al. JPT (1995) 782–787.*
McClements, David J. J. Acoust. Soc. Am. vol. 91 (Feb. 1992) 849–853.*
McClements et al. Ultrasonics vol. 30 (1992) 383–388.*
de Boer et al. SPE Production and Facilities (Feb. 1995) 55–61.*
McClements, David Julian Adv. Coll. Interfac. Sci vol. 37 (1991) 33–72.*

* cited by examiner

*Primary Examiner*—Michael Cygan
(74) *Attorney, Agent, or Firm*—Thompson Coburn LLP

(57) ABSTRACT

A method is provided for measuring the agglomerative state of asphaltenes in oil by applying an acoustic signal to the oil, detecting the scattered acoustic energy and using this detected signal to determine the relative particle size distribution of the asphaltene particles in the oil and/or their state of agglomeration. A method for controlling the agglomerative state of the asphaltenes which is based on the acoustic measurement technique is also provided.

22 Claims, 10 Drawing Sheets

MEASUREMENT AND CONTROL OF ASPHALTENE AGGLOMERATION IN HYDROCARBON LIQUIDS

This is a continuation-in-part of Application No. 08/947,821, filed on 09 Oct. 1997.

BACKGROUND OF THE INVENTION

1. Field of the Invention

The present invention relates to asphaltene-containing liquid hydrocarbons and, more particularly, to measurement and/or control of the agglomeration of asphaltenes in hydrocarbon liquids.

2. Description of the Related Art

Asphaltenes are organic heterocyclic macromolecules which occur in crude oils. Under normal reservoir conditions, asphaltenes are usually stabilized in the crude oil dispersion by maltenes and resins that are chemically compatible with asphaltenes, but that have much lower molecular weight. Polar regions of the maltenes and resins surround the asphaltene while non-polar regions are attracted to the oil phase. Thus, these molecules act as surfactants and result in stabilizing the asphaltenes in the crude. However, changes in pressure, temperature or concentration of the crude oil can alter the stability of the dispersion and increase the tendency of the asphaltenes to agglomerate into larger particles. As these asphaltene agglomerates grow, so does their tendency to precipitate.

Precipitation of asphaltenes in crude oil or in process streams of oil is economically costly because of lost production and maintenance required to clear blockages caused by the solid materials.

Various methods have been devised to minimize asphaltene precipitation. For example, pressure and temperature conditions can be maintained, chemical stabilizers may be added to mimic and to enhance the stabilizing affect of the natural resins and maltenes, or devices such as magnetic flux assemblies described in U.S. Pat. No. 5,453,188 may be used. While methods that minimize asphaltene precipitation can result in significant economies, they have been hampered by a lack of a method for measuring and monitoring the agglomerative state of the asphaltenes in a particular stream at a particular time. Without knowing the agglomerative state of the asphaltenes in the stream, it is unclear when or how much to treat the liquids to prevent asphaltene precipitation.

Conventional methods for determining the size and concentration of asphaltene particles in hydrocarbons, such as those described in U.S. Pat. No. 4,238,451, or in Standard Method IP 143/84, require sampling, transport to a laboratory and testing by precipitation and filtration, centrifugation, titration with a destabilizing solvent, or other lengthy and involved techniques. Thus, these methods are time consuming and destructive of samples when used in bench-scale or laboratory settings and are not suitable for real-time, on-line monitoring of agglomeration.

Although methods for testing for the size and concentration of particles in optically clear streams have been modified and applied to hydrocarbons, many have been much less successful in crude oil and other in-process oil streams due to fouling and opacity. For example, the optical system of Yamazoe, et al., U.S. Pat. No. 4,843,247, measures asphaltene content, but provides a washing means to remove the sample solution from the optical probes each time a sample measurement is carried out. Such washing requires more complex measuring devices and infers that fouling over time may hinder the accuracy of the optical measurement.

Direct centrifugation of crude oil measures the total amount of asphaltene present, but provides no information of the size and degree of agglomeration of the particles or their tendency to remain in a stable dispersion.

Non-optical tests have recently shown promise in measuring particle characteristics. Anfindsen et al., U.S. Pat. No. 5,420,040 correlated the precipitation of asphaltenes in oil with changes in conductance or capacitance. However, this method requires transferring a sample of the liquid to be measured to a measuring cell and is not carried out on-line. Furthermore, the process is carried out stepwise and cannot be done substantially instantaneously size a time delay is required to allow for the precipitation of asphaltenes to occur.

Behrman and Larson, *MBAA Technical Quarterly*, 24, 72–76 (1987), describe on-line monitoring of particles over 0.8 microns in brewery streams by the use of an ultrasonic monitoring device. They use a piezoelectric transducer to generate an acoustic signal and to detect acoustic energy resulting from scattering from particles in the liquid streams. The device permitted on-line, real time measurement of particle concentrations, but did not permit the measurement of particle sizes or a particle size distribution.

More recently, Lin, et al., "Neutron Scattering Characterization of Asphaltene Particles", presented as ACS National Meeting, San Francisco, Calif. April 1997, reported the use of small-angle neutron scattering (SANS) to determine the size and concentration of asphaltene particles in dilute solution in 1-methyl-naphthalene-D10. The study concentrated on small, "basic", asphaltene particles and reported that larger particles, which might be important to macroscopic properties, could not be measured by today's small angle scattering instruments and would be very difficult, if not impossible, to measure with light scattering methods.

de Boer, et al., *SPE Production & Facilitates*, pp. 5–61, February (1995), reported the investigation of asphalt precipitation in oils and describe using back-scattered energy from an acoustic probe to sense asphaltene particles. A multi-channel analyzer was used to sort the signals into two amplitude classes corresponding to small and large particle sizes. The acoustic sensing procedure was used to monitor the relative numbers of large and small particles during heptane titration of the oil to induce asphalt precipitation. Since the method required the addition of significant amounts of n-heptane to the oil, it would be impractical to apply the test to an in-process stream or on a real-time basis. Furthermore, the titration procedure required significant time to complete for each sample and would not readily lead itself to the rapid measurement of the agglomerative state of asphaltenes in a laboratory. The publication did not disclose a method of interpreting the scattered acoustic energy measurements without the addition of n-heptane to initiate precipitate and provided no reason for doing so.

Later, a group from the same laboratory reported the laboratory use of the same ultrasonic particle analyzer to study the utility of asphaltene inhibitors. (Bouts, et al., *J. Petr. Tech.*, 782–787, Sep. 1995). The method included a test cell attached to a sonic probe which acted as described above to measure the energy scattered from particles in the liquid. A multichannel analyzer counted particles and sorted the detected scattered energy into thirteen amplitude classes. The two channels measuring the smallest particles and the remaining 11 channels measuring larger particles were respectively lumped together to monitor "small" and "large"

particles versus time as the sample was titrated with n-heptane to destabilize the asphaltenes. The purposes of the method was to test various inhibitors by monitoring the formation of asphaltene agglomerates as a function of the heptane added and the inhibitor content. The study did not show how to interpret or use particle size distribution data for more than two particle size ranges or without the addition of heptane. Furthermore, the article did not disclose how the agglomerative state of asphaltene particles in a hydrocarbon liquid could be determined on a real-time basis, without dilution, or without removing a sample of the liquid from the stream or tank in which it is contained.

Thus, despite progress with promising techniques in related areas, a suitable method has not been available to measure the agglomerative state of asphaltenes in oils, such as a crude oil or any other optically opaque hydrocarbon liquid rapidly and without sample dilution in a laboratory setting, or on a real-time basis and without diluting or removing a sample from the process stream. The lack of such method has also limited the ability to control the agglomeration of asphaltenes in such oils.

BRIEF DESCRIPTION OF THE DRAWINGS

Corresponding reference characters indicate corresponding parts throughout the several views of the drawings.

SUMMARY OF THE INVENTION

The present invention, therefore, is directed to an improved methods for measuring the agglomerative state of asphaltenes in oil containing asphaltenes, comprising applying to the oil a signal of acoustic energy, thereby scattering at least part of the energy; detecting the scattered acoustic energy over a selected frequency range; resolving the magnitude of the detected scattered acoustic energy at selected frequencies within the selected frequency range; and determining the agglomerative state of the asphaltenes. This method can be used to measure the agglomerative state of oil in a process flow stream or in a small sample that has been removed from the bulk of the oil.

Further, the inventors provide a method for determining the agglomerative state of asphaltenes in an oil containing asphaltenes comprising removing a sample of the oil and without diluting the oil; applying to the oil a signal of acoustic energy, thereby scattering at least part of the energy; detecting the magnitude of the scattered acoustic energy over a selected frequency range; resolving the magnitude of the detected scattered acoustic energy at selected increments within the selected frequency range; deriving from such resolution a distribution of the relative size of asphaltene particles scattering acoustic energy within the selected frequency range; and determining the agglomerative state of the asphaltene particles. Optionally, the sample may be returned to the bulk of the oil. Also provided is a method for controlling the agglomeration of asphaltenes in oil which comprises applying a signal of acoustic energy to the oil, thereby scattering at least a part of the energy; detecting the scattered energy over a selected frequency range; resolving the magnitude of the detected scattered energy at selected increments within the selected frequency range; comparing the resolved detected scattered energy with a standard; and acting to control the number of particles having a particle size corresponding to the selected incremental frequencies.

Among the several advantages of this invention may be noted the provision of a method for the determination of the agglomerative state of asphaltenes in an oil, such as a crude oil or a process stream of hydrocarbon liquid, on a real-time basis; the provision of such method that can be conducted either in-line, without removing a sample from the process stream, or upon a sample of the oil that has been removed from the bulk of the coil; the provision of a method that does not require dilution of the oil or addition of another material to the oil; and the provision of such method that facilitates the control of the agglomeration of asphaltenes in oils.

DETAILED DESCRIPTION OF THE PREFERRED EMBODIMENTS

In accordance with the present invention, it has been discovered that the concentration and distribution of relative sizes of asphaltene particles in oil can be measured in real-time by applying a signal of acoustic energy of the oil, thereby causing at least some part of the signal to scatter as it encounters asphaltene particles within the oil, and detecting the scattered acoustic energy over a selected frequency range. The magnitude of the detected scattered acoustic energy may be resolved at selected frequencies within the selected frequency range. If desired, a distribution of the relative size of asphaltene particles which scattered acoustic energy within the selected frequency range may be calculated from the magnitude vs. frequency data by correlating the measured data with a known standard or a model. Whether or not the magnitude vs. frequency data is correlated with a particle size distribution, the agglomerative state of the asphaltene particles in the oil may be determined by comparing the magnitude vs. frequency data, or the particle size distribution, with a standard so that differences between the two indicate the state of the asphaltene particle agglomeration in the oil. As used herein, the term "agglomerative state" means the relative particle size distribution and is meant to include data that, upon correlation with a known standard or model, will yield such relative particle size distribution.

Actions for controlling asphaltene agglomeration in the oil then may be based on such measurement. In one embodiment of the invention, moreover, the use of, for example, an oscilloscope and computer to resolve the detected scattered energy quickly into magnitude at each of a large number of frequencies and to device a relative particle size distribution permits the measurement to occur on a real-time basis. Also, because the determination of the agglomerative state of the asphaltene can be carried out without titration, or other modification or dilution of the liquid being tested, the method can be used in-line, and without diluting, or otherwise contaminating, the process flow stream or any samples that may be taken.

In the present application, the term "oil" is meant to include crude oil and any other liquid hydrocarbon. While the method of the present invention may be used on any oil, it is more advantageously used on an oil which contains asphaltenes and is most advantageously used on oils that are optically opaque.

Figure 1:
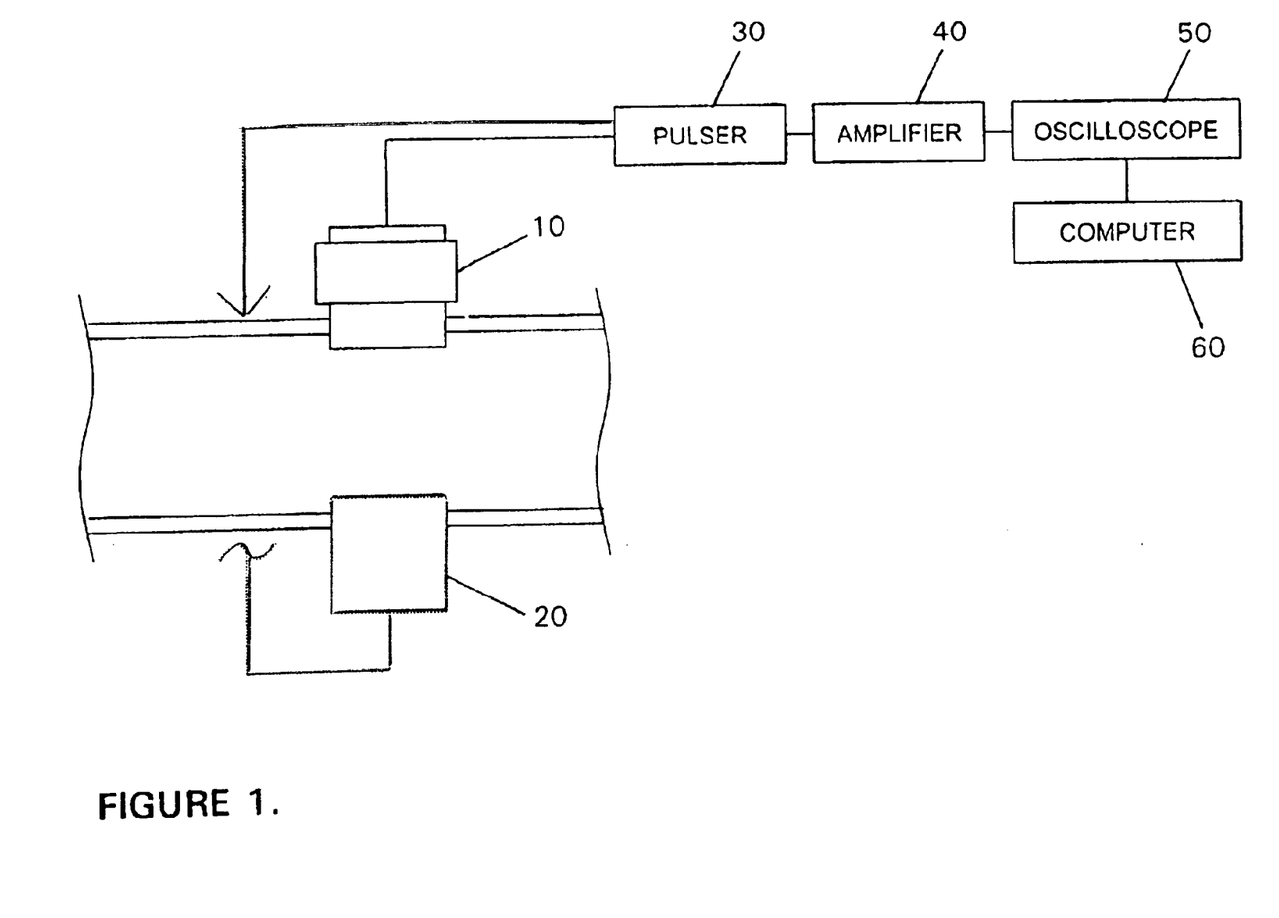
FIG. 1 is a block diagram of the components of system that may be used to practice an embodiment of the present invention.

A system that may be used to practice the present invention is shown in the block diagram of FIG. 1. In general, a pulse generator, or pulser 30, generates an electrical signal which is transmitted to an acoustic probe 10 that transduces the electric signal into an acoustic signal that is transmitted into the oil that is to be tested. The same probe, or, optionally, a separate sensor 20, detects an "echo" of the acoustic signal which is caused by scattering of the signal as it encounters asphaltene particles in the oil. An amplifier 40 amplifies the detected scattered signal and transmits the amplified signal to an oscilloscope 50 which converts the signal from analog to digital, selects that part of the detected scattered signal that results from scattering in the focal region of the probe (which selection step is termed "gating"), and transforms the amplitude vs. time signal into a magnitude vs. frequency distribution. This distribution is transmitted to a computer 60 that compares the distribution with a standard and determines the agglomerative state of the asphaltenes in the oil.

As would be readily recognized by one of ordinary skill in the art of ultrasonic measurement, the system described above could be easily modified while still carrying out the same functions. For example, the electric signal to be transmitted to the probe 10 could be generated by the oscilloscope 50, or a combined pulser/amplifier, as well as by the pulser 30. Alternatively, the oscilloscope 50 could provide amplification of the sensed signal and replace the separate amplifier 40. Likewise, if desired, the computer 60 could accomplish the calculation functions ascribed above to the oscilloscope 50. Other systems for the ultrasonic measurement of particles in liquids are generally described in U.S. Pat. No. 4,412,451 to Uusitalo et al., U.S. Pat. No. 4,509,360 to Erwin et al., U.S. Pat. No. 4,706,509 to Riebel, and U.S. Pat. No. 5,121,629 to Alba.

The various parts of a system to practice the present invention and their operation are described as follows.

The acoustic probe 10 can be a focused ultrasonic transducer that applies a signal of acoustic energy into the oil. The probe includes, in general, a piezoelectric crystal capable of transforming electrical signals into physical pulses. If the crystal is in contact with a fluid, such physical pulses are transferred to the fluid and initiate waves having a frequency that is controlled by the frequency of the electronic signal. Preferably, the probe 10 also contains a lens to focus the signal as illustrated by the dashed lines of FIG. 2. The focal length of the probe 10 is the distance from the end of the probe to the point where the wave patterns converge. The point where the wave patterns converge is sometimes termed the "focal region". While focal length is not critical, it is preferable for the focal length to be less than the distance form the lens of the probe 10 to any opposing pipe or tank wall, or opposing wall of a measuring cell; i.e., the focal region should be within the fluid of interest. A probe 10 having a focal length of about 100 mm is suitable for the present invention as long as no wall, pipe or other process equipment structure intervenes between the probe 10 and the focal region.

As used herein, the terms "probe", "sensor" and "transducer" mean the same thing and are sometimes used interchangeably. Of the word "probe" is used to describe a transducer when it is used primarily to transmit a signal and "sensor" is used when the transducer is used primarily to receive or sense a signal.

The acoustic probe 10 should be capable of sending an acoustic signal having a duration, amplitude and frequency range suitable for the invention. Such signal may be a pulse or a "tone-burst".

If the signal is a pulse, it can be transmitted to the probe 10 as a high-voltage spike of short duration and typically repeated many times per second. For example, a 5 MHz probe that can transmit a 10 nanosecond (ns), 300 volt signal is suitable for some applications of this invention. However, a 10 MHz probe is preferred, while a 100 MHz probe is more preferred and a 200 MHz probe is most preferred.

If the signal is a tone-burst, it can be directed into the oil in place of the spike, or pulse, just described. The tone-burst sweeps through the frequency spectrum selected for use and each frequency is detected and analyzed separately. The tone-burst will preferably have a duration of between 4 and 8 cycles. The actual time of the duration will depend on the period (T) of the tone. If there are (n) cycles in the tone, then the duration will be nT.

Typical operation of an acoustic probe and ultrasonic systems similar to those suitable for use in the present invention is described, for example, by Urick, R. J., *J. Appl. Phys*, 18, 983–987 (1947); McClements, D. J., et al., *J. Phys. D: Appl. Phys.* 22, 38–47 (1989); Holmes, A. K., et al., *J. Coll. Int. Sci.* 156, 261–268 (1993); McClements, D. J., *Adv. Coll. Int. Sci*, 37, 33–72 (1991); McClements, D. J., *J. Acoust. Soc. Am.* 91, 849–853 (1992); Pinfield, V. J., et al., *J. Coll. Int. Sci.* 166, 363–374 (1994) and McClements, D. J., The use of ultrasonics for characterizing fats and emulsions, Ph.D. Thesis, Food Science Department, University of Leeds, UK (1988); each of which is hereby incorporated by reference.

The probe should be capable of resisting temperature to 200° C., and preferably to 300° C., and most preferably to 500° C. The probe should also be capable of resisting pressure to about 10 Pa, and preferably to about 250 Pa and most preferably to about 500 Pa. Moreover, the probe should preferably be capable of resisting chemical corrosion and physical erosion by the oils in which it is to be used.

Suitable probes may be commercially obtained or may be fabricated. One type of commercially available acoustic probe suitable for use in the present system is a barium-titinate ceramic 10 MHz probe as supplied with a Balteau-Sonatest UFD-1 ultrasonic tester.

Figure 10:
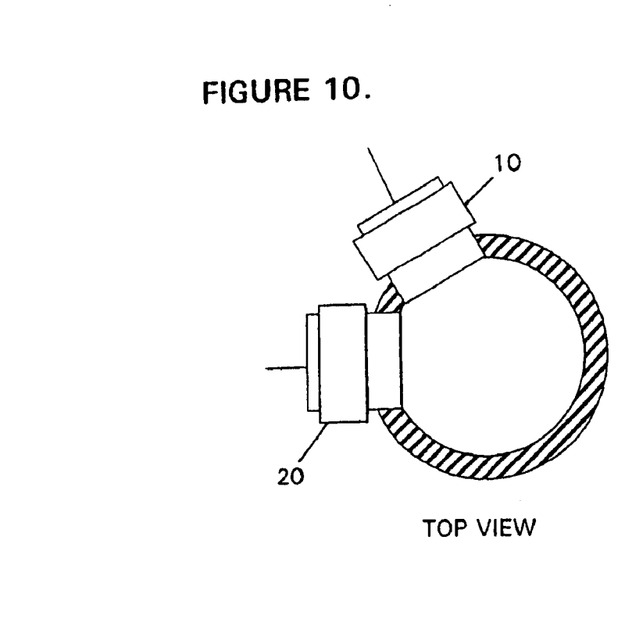
FIG. 10 is a top view of a measuring cell having two transducers adapted for bench-scale or laboratory use for practicing an embodiment of the present invention.
Figure 11:
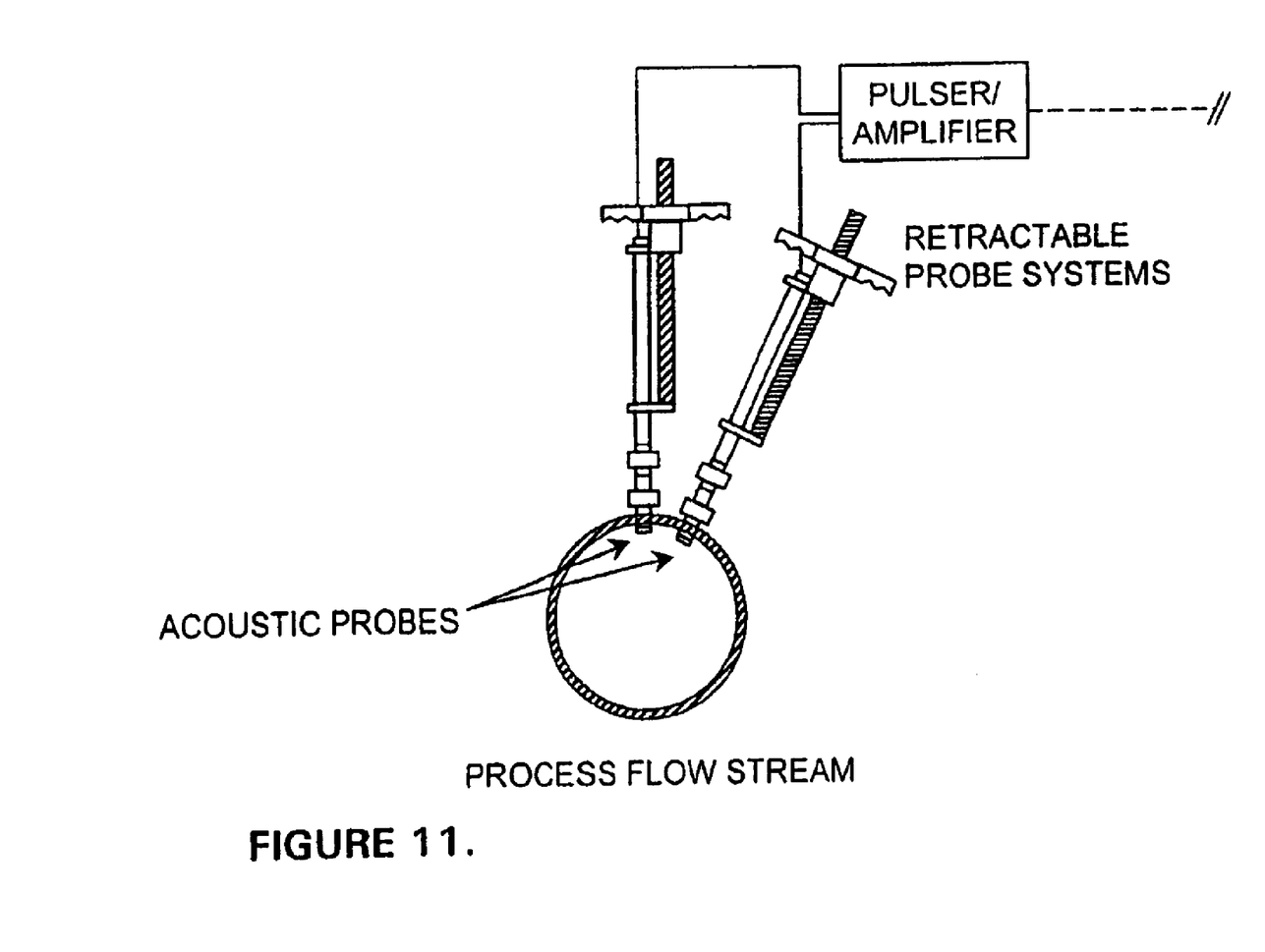
FIG. 11 is a diagram of a system which may be used in held applications of the present invention wherein two acoustic probes are shown in a cross-section view of a pipe where each acoustic probe is mounted through the pipe wall in a retractable system.

In one embodiment, the acoustic probe 10 may also be used as a sensor to detect acoustic energy scattered by particles in the oil. Only one transducer is required for this arrangement and the same transducer serves as the signal input probe and the sensor. Alternatively, an input probe 10 can be used with one or more separate sensors 20. Referring to FIGS. 1, 10 and 11, if a separate sensor 20 is used, it may be placed anywhere in the fluid in relationship to the probe 10, but close enough to receive energy scattered from the focal region. However, the probe 10 and the sensor 20 cannot touch each other. In FIG. 10, the separate probe 10 and sensor 20 are shown as mounted in a sample measuring cell as might be used in a bench-scale or laboratory system. In FIG. 11, the separate probe 10 and sensor 20 are shown as being mounted in retractable probes as might be suitable for in-line mounting in a pipe carrying a process flow stream. Although a separate sensor 20, if one is used, can be placed almost anywhere in the fluid in relation to the probe 10, it is preferred that the sensor be located near the probe, but mounted so that the signal direction of the probe intersects the signal direction of the sensor at or near the focal region of each at an angle of less than about 90°. When it is said that the sensor is located "near" the probe, it is meant that the sensor is located so that it is capable of sensing backscattered energy caused by the input signal of the probe. Preferably, the sensor is located within about two meters of the probe, more preferably within about one meter and even more preferably within about 0.25 meters of the probe.

Figure 2:
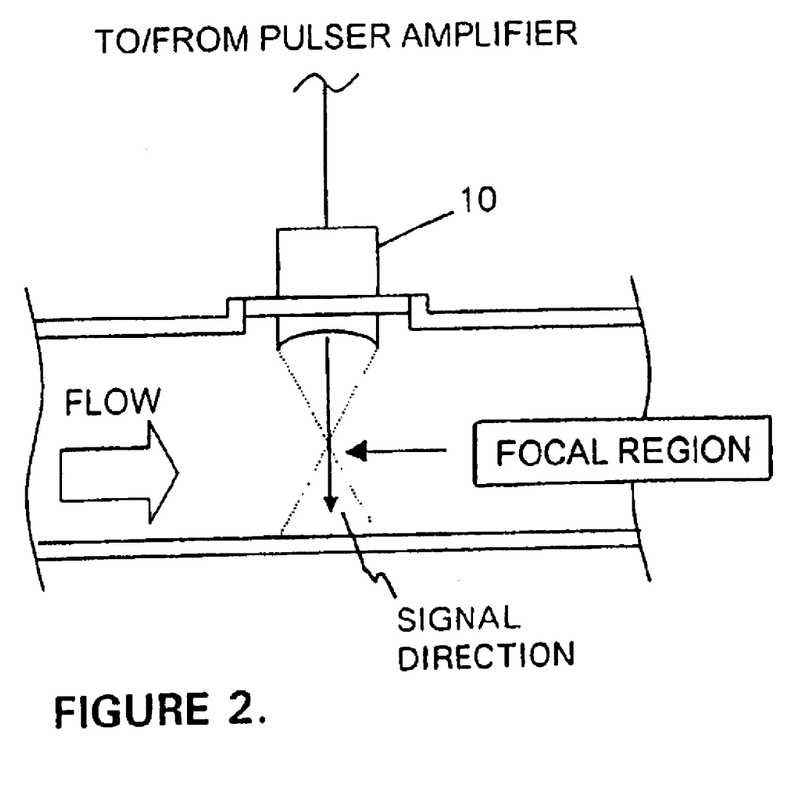
FIG. 2 shows a diagram of a focused acoustic probe mounted in a pipeline wherein liquid flow direction is indicated by the arrow and the focal region of the acoustic signal is indicated by the intersection of the dashed lines.

As used herein, the term "signal direction" is meant to mean the direction perpendicular to any away from the face of a transducer, which direction lies along a line that passes from the center of the active face of the transducer through the focal region for that transducer, such as shown, for example, in FIG. 2. The active face of a transducer is that part of a transducer through which acoustic signals are exchanged with the fluid with which the transducer is in contact. An advantage that is gained by using a separate probe and sensor is that the probe and sensor can be located so that the input signal generated by the probe does not interfere with the backscattered energy signal sensed by the sensor. Because the backscattered energy signal is often significantly lower in strength than the input the signal, removal of the input signal interference permits cleaner and more sensitive reception of backscattered energy by the sensor. Moreover, the lack of interference by the input signal permits the signal handling and interpretation process to be simplified, as will be discussed below. It is preferred that the probe and the sensor are located so that the signal direction of the probe intersects the signal direction of the sensor at an angle of less than about 90°, more preferably at an angle of less than about 60° and most preferably at an angle of less than about 45°. By way of example, assuming that the probes and sensors shown in the figures are in the same plane, the signal direction of the probe 10 shown in FIG. 1 apparently intersects the signal direction of the sensor 20 at an angle of about 180°, while the signal directions of the sensor and probe of FIG. 10 apparently intersect at an angle of about 60° and the signal directions of the sensor and probe of FIG. 11 intersect an at angle of about 28°. It should be noted that the actual intersection of the signal directions of the probe and sensor is not required for the invention to be operable. Rather, such description is merely used to indicate the preferred location of the probe and sensor.

The sensor, whether it is the probe 10, or a separate sensor 20, converts the acoustic waves of the scattered acoustic energy encountering the piezoelectric crystal to an electrical signal. Operation of an acoustic energy sensor, in general, is described by the references given above in the section describing the probe 10.

It is preferable that the sensor of the subject system has sensitivity suitable for sensing back-scattered energy having frequencies up to 20 MHz, but a probe which can sense back-scattered energy having frequencies up to 100 MHz probe is more preferable and a probe which can sense back-scattered energy having frequencies up to 200 MHz probe is most preferable.

Figure 3:
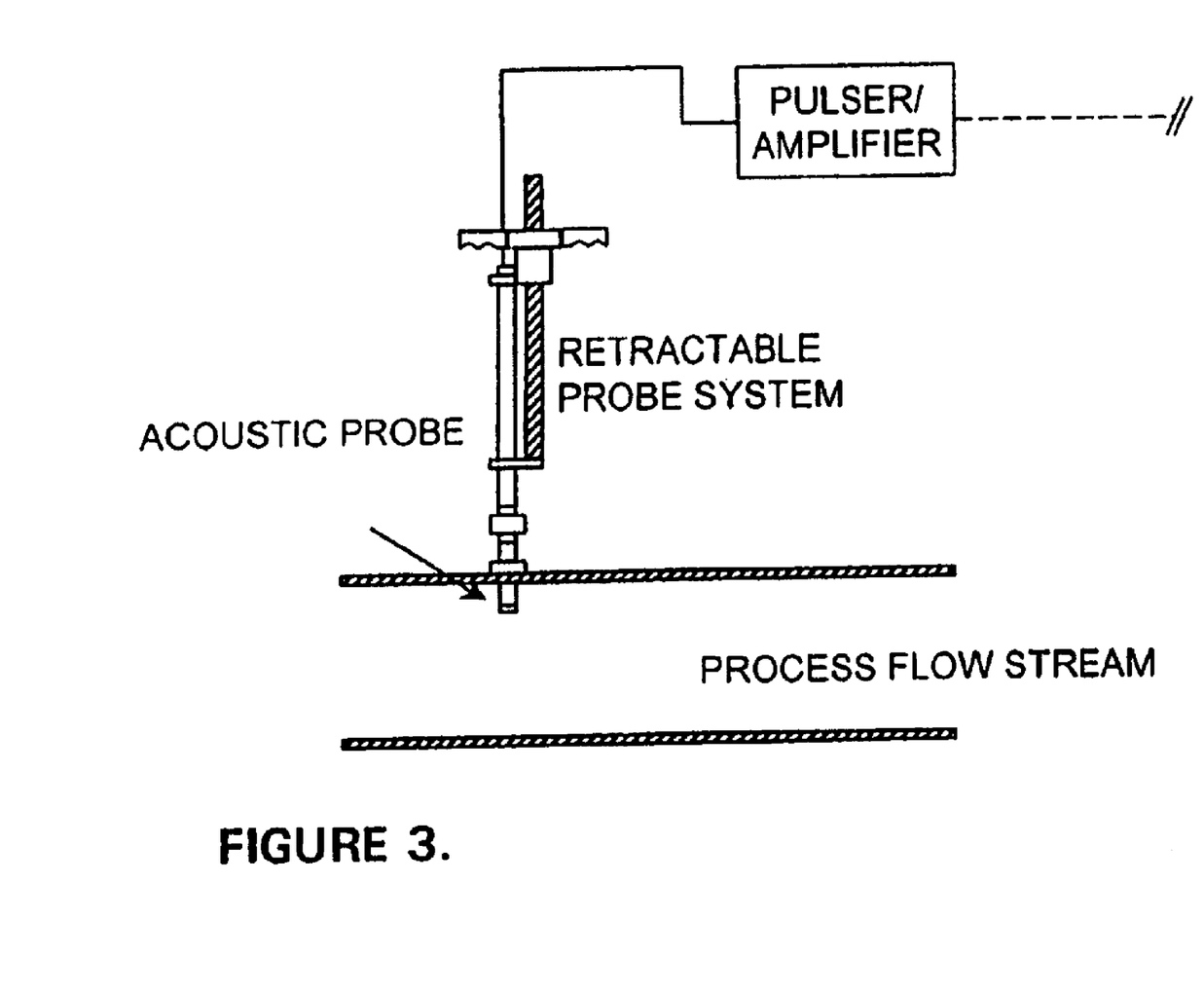
FIG. 3 shows a diagram of a system which may be used in field applications of the present invention wherein the acoustic probe is shown mounted in a retractable system.

The acoustic probe 10 may be mounted in a retractable mounting, as shown in FIG. 3 and FIG. 11, for controlled insertion of the probe into a pipeline or a tank. The retractable mounting permits the probe 10 to be easily withdrawn from contact with the liquid for maintenance or replacement without dismantling the tank or line. The retractable mounting may be manually activated, or may be motor driven. The design of the mounting that is used for the probe 10 is not critical and any technician of ordinary skill would be able to design a suitable mounting.

A pulser 30 provides the necessary input signal to drive the transducer of the probe 10. As mentioned above, the oscilloscope 50 can also be used to generate the input signal.

An amplifier 40 amplifies the detected scattered signal before it is transmitted to the oscilloscope 50. The pulser 30 and amplifier 40 may be separate components or may be combined in a single component. For example, a UTEX UTP320, from UTEX Scientific Instruments, Inc., provides both pulser 30 and amplifier 40 functions in a combined component.

The oscilloscope 50 of the present system should be capable of gating the scattered acoustic signal, carrying out an analog to digital conversion and, preferably, transforming the signal from an amplitude vs. time format to a magnitude vs. frequency format. The gating function limits the signal to the detected energy scattered by particles within the focal region (region "B" in FIG. 4). Thus, it deletes that part of the signal due to the input pulse (region "A" in FIG. 4), any reflection due to an opposing pipe wall and all other portions of the signal except for the scatter due to particles in the focal region. When a separate probe 10 and sensor 20 are used in a preferred configuration as described above, the sensor 20 does not sense any part of the signal due to the input pulse. Thus, the gating function is not required for a system having separate probe and sensor that are located in a preferred configuration.

Oscilloscopes that are suitable for use in the present system are, for example, a LeCroy Model 9540 and a LeCroy Model 9320. Such oscilloscopes should be complete with software suitable for waveform processing such as, for example, Waveform Processing Packages One and Two, available from LeCroy. Date from the oscilloscope is transferred to a computer 60 by using, for example, a National Instruments IEEE Plug and Play adapter.

A computer 60 is used in the present system to receive the signal from the oscilloscope 50 and to the store the waveforms for future reference and also to compare the waveforms against reference scans and other standards, to perform particles size modeling and analysis, to determine the agglomerative state of the asphaltenes in the oil and to initiate nay desired alarm or control action.

While the type and computational speed of the computer are not critical, it is preferred that a personal computer having a Pentium7 processor, or its equivalent, and having spread sheet software such as, for example, Microsoft Excel7, be used in the present system.

The several components of a system suitable for practicing the present invention should be interconnected as indicated in FIG. 1 and to other necessary electrical sources or components to enable the proper and intended operation of each component. In general, the probe 10 should be connected so as to receive an input electrical signal from the pulser 30 and to transmit a detected scattered acoustic signal to the amplifier 40. The amplifier 40 should be connected to transmit an amplified scattered acoustic signal to the oscilloscope 50. The oscilloscope 50 is connected to the computer 60 so that, after performing necessary gating and transforming steps, it can transmit data to the computer 60 for further calculations resulting in the determination of the agglomerative state of the asphaltenes and the initiation of any desired alarm or control functions.

The present method for measuring the agglomerative state of asphaltenes in oil containing asphaltenes is carried out by applying to the oil a signal of acoustic, or ultrasonic, energy. The present method is capable of determining the agglomerative state of asphaltenes in almost any oil that contains asphaltenes, but is especially useful for crude oil, other optically opaque streams, or streams and samples where other in-line, real-time sensing methods can not operate because of high pressures or high temperatures.

In one embodiment, the method of the present invention can be applied to oil in a process flow stream under real-time conditions. In this application, the acoustic signal is preferably applied to an oil for which the agglomerative state is to be determined before any dilution of the oil that may be involved in the processing (e.g., refining) which the oil is to undergo and without diluting or adulterating the oil during the application of the signal. The acoustic probe 10 is most preferably installed on the reactor, vessel, exchanger, pipeline, tank or other container or conduit in which the oil is being stored, transferred, or processed so that the signal may be applied to the oil in the process flow stream and without removing the oil from such process flow stream, thereby avoiding disruption of or interference with the storage, transfer or process to which the oil is being subjected.

The term, "process flow stream", as it is used herein, means any stream or bulk amount of oil that is not a small sample and is meant to include oils in pipelines, reactors, heat exchanges, tanks, pumps, pipes, lines, or any other container or conduit in which oil is conventionally stored, handled, processed, transported, or transferred to, from or during processing or storage, but is not meant to include small samples of oil which have, for testing purposes, been removed from or separated from a bulk amount of the oil for which the agglomerative state of asphaltenes is to be measured or controlled.

When it is said that a test, probe, or instrument is applied, "in-line", it means that the test, probe, or instrument of interest is applied directly in the process flow stream, rather than to a sample of such stream.

The acoustic signal should be applied to the liquid as a pulse or a continuing series of pulses, or as a tone-burst. The frequency range of the acoustic signals of most interest in the present method is roughly from 0.1 MHz up to about 200 MHz.

Acoustic waves are reflected when they hit an interface between the liquid and a discontinuity such as a particle. As the acoustic signal propagates through the liquid, it encounters whatever particles are in its path. When a focused acoustic probe is used, the acoustic signal converges in a focal region creating a particularly strong signal at that point. When the signal encounters a particle, some of the acoustic energy is scattered. Particles of different size cause energy to be scattered at different frequencies. Furthermore, the more particles present in the path of the signal, the greater the amount of the acoustic energy that is scattered. Therefore, a particular distribution of size and number of particles in a liquid results in scattered acoustic energy characteristic for both the size and number of the particles. Since crude oils and other in-process oils are largely free of microscopic particles other than agglomerates of asphaltenes, the particle size distributions obtained from the acoustic scattering technique corresponds to the distribution of asphaltene particles.

The scattered acoustic energy is detected by a sensor or detector described above. While the probe 10 may also act as the sensor for back-scattered energy, separate sensors 20 may be placed relative to the signal probe, as described above, to detect forward scatter, or energy scattered at any other angle. The detection of back-scattered energy is preferred from some embodiments for adaptation to an on-line device because, for example, one probe can act as both signal probe and sensor.

When asphaltenes agglomerate to form particles, the first particles formed may be relatively small, perhaps comprising only a few asphaltene molecules. However, if conditions persist which favor agglomeration, the asphaltene particles grow. It is important, therefore, that the scattered acoustic energy be detected in a frequency range that includes the frequencies characteristic for energy scattered by the particular asphaltene particles in the oil. The inventors have discovered that this characteristic frequency range may vary with the type of oil and type of process being imposed upon the oil. Measuring scattering energy over the wrong frequency range may entirely miss any asphaltene agglomerates that form. Thus, a characteristic frequency range may have to be calibrated and optimized for each installation of the system. As long as one is aware of the need to determine a suitable frequency range, this can be easily done by one skilled in the art without undue experimentation.

Detection of scattered acoustic energy over a frequency range of from about 0.1 MHz to about 20 MHz is suitable for determining the state of agglomeration of asphaltenes in a typical oil, but, in order to insure the detection of a wider range of particle sizes, detection over a frequency range of from about 0.1 MHz to about 100 MHz is more preferable and detection over a frequency range of from about 0.1 MHz to about 200 MHz is most preferable. However, once the frequency range characteristic for energy scattered by the particular asphaltene particles in a particular oil has been determined, it may be useful to detect scattered energy only over, or within, this more limited range.

Figure 4:
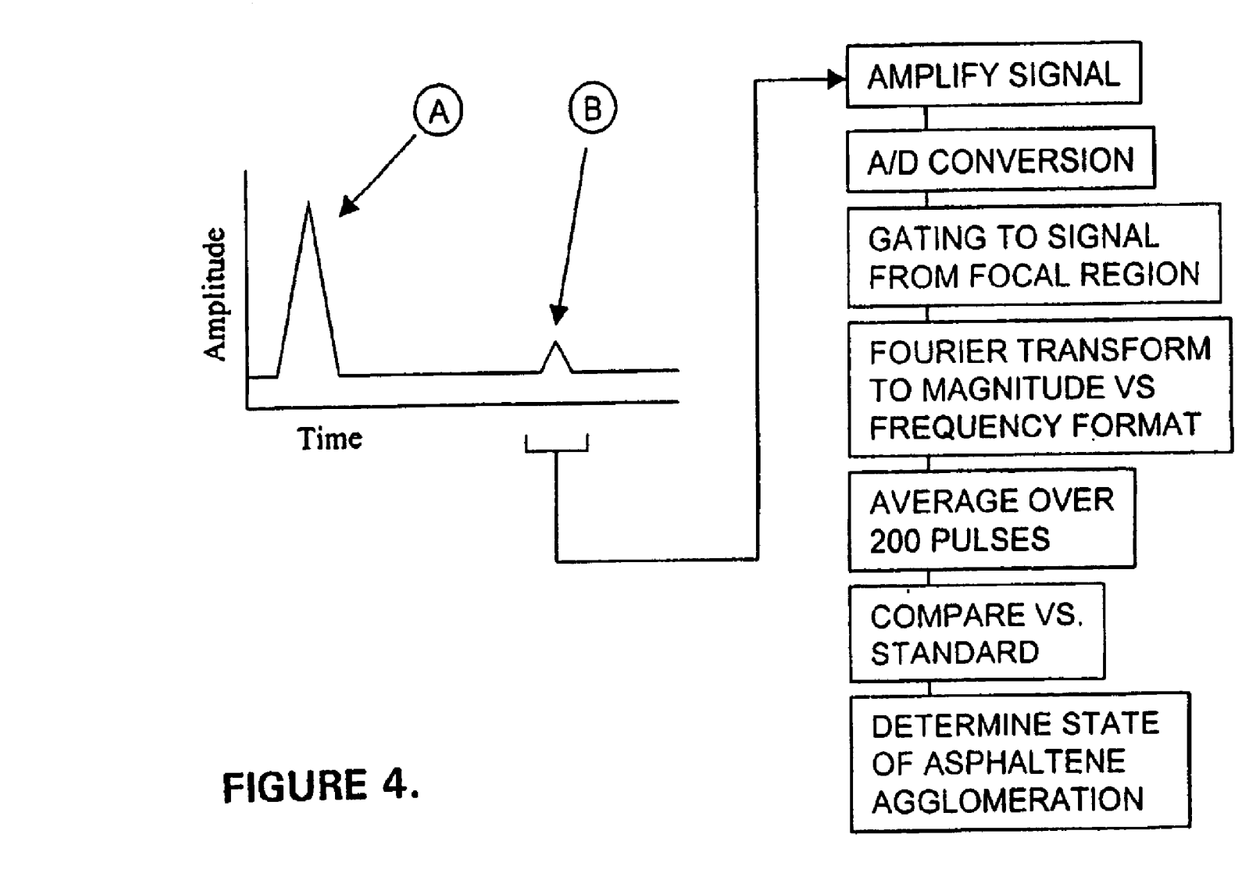
FIG. 4 is a block diagram of a system that may be used in the present invention to acquire and transform the scattered acoustic signal into a magnitude vs. frequency format.

If a spike, or pulse, input signal is used, the echo, or scattered signal, is detected as an amplitude vs. time plot resulting from each such input pulse, as illustrated in FIG. 4. This plot of the amplitude of the detected scattered signal received from each pulse vs. time shows the detected signal as a spite at time=0, indicative of the input pulse itself, and, thereafter, the sensor detects acoustic energy scattered by material in the path of the acoustic wave. The distance along the "time" axis corresponds to distance from the end of the probe because the time required for a wave to hit a particle and reflect back into the probe is controlled by the speed of sound in the oil and the distance of the particle from the end of the probe.

The amplitude of the detected energy is proportional to the concentration of the particles in the path of the signal. A particularly strong response is received from the focal region due to convergence of the input signal at that point.

The signal received by the sensor is amplified using a narrow band amplifier and tuned to match the transducer fundamental frequency. If a single probe is used, the signal is gated to focus on scattering from the focal region and can then be converted into a digital signal by an analog/digital converter. If separate probes are used to generate the input signal and to sense the backscattered energy, the gating step can be avoided when the probe and sensor are located in a preferred configuration, as previously described.

The amplified, converted signal is then resolved into a magnitude vs. frequency format so that the relative particle size distribution may be correlated and the state of agglomeration of the asphaltenes may be determined. Methods for carrying out this resolution are described by McClements, D. J., et al., *Ultrasonics*, 31, 433–437 (1993); McClements, D. J., et al., *J. Coll. Int. Sci.*, 160, 293–297 (1993); Dickenson, E., et al.,*J. Coll. Int. Sci.*, 142, 103–110 (1991); and McClements, D. J., and M. J. W. Povey, *Ultrasonics*, 30, 383–388 (1992); which references are hereby incorporated by reference.

Figure 5:
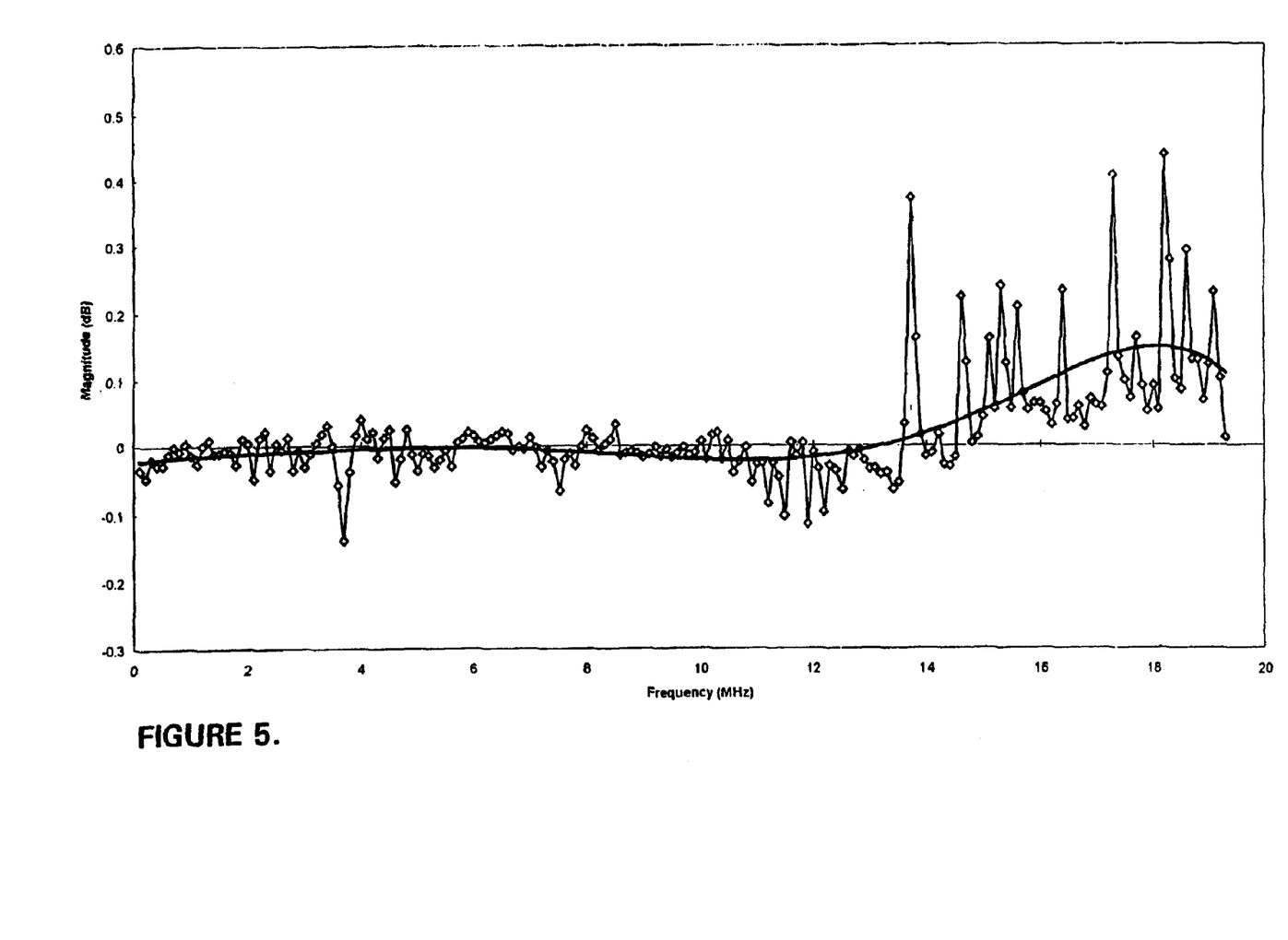
FIG. 5 is a magnitude vs. frequency plot of detected back-scattered acoustic energy in an undiluted untreated crude oil within a frequency range of about 0.01 MHz to about 20 MHz.
Figure 6:
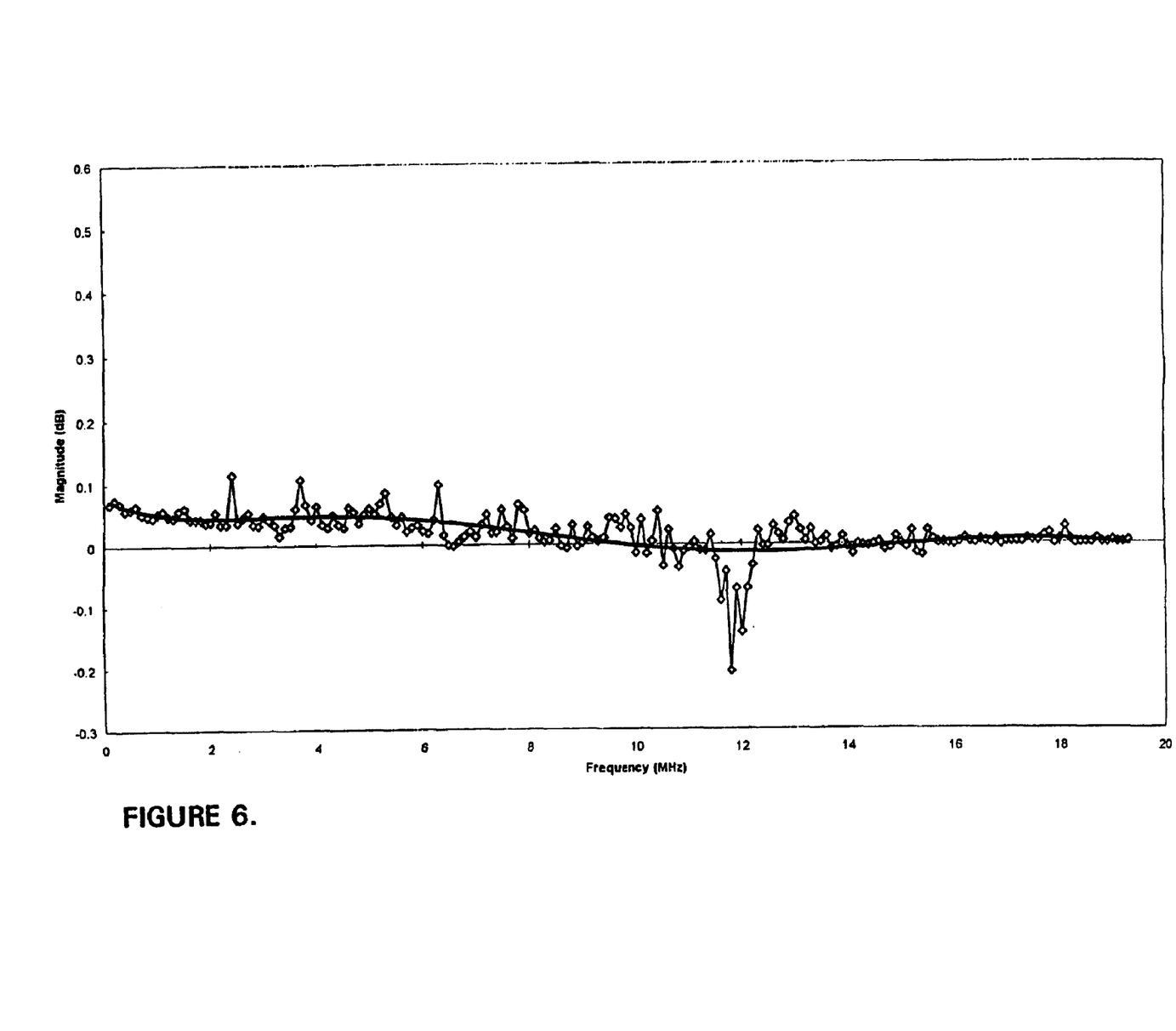
FIG. 6 is a magnitude vs. frequency plot of detected back-scattered acoustic energy within a frequency range of about 0.01 MHz to about 20 MHz in an undiluted crude oil that has been treated to suppress the formation of asphaltene particles.

The amplified, gated (if necessary) and converted signal is transformed from an amplitude vs. time format into a magnitude (decibels, dB) vs. frequency (MHz) format by Fourier transformation. The magnitude vs. frequency data is then averaged, preferably over about 200 pulses, and exported either to the oscilloscope or computer screen for display as a magnitude vs. frequency plot, as shown in FIG. 5 and FIG. 6, or to the computer for storage and further computations.

Once the detected signal is resolved into magnitude versus frequency data, a distribution of the relative size of asphaltene particles scattering acoustic energy within the selected frequency range can be derived, if desired. This derivation may be done by correlating the frequency, at any specific frequency within the frequency range of interest, with a particular known particle size. This may be done by obtaining the frequency response data for standard mixtures containing particles of known sizes, or by prediction of a frequency vs. particle size correlation model based on scattering theory. Comparison against a known standard has been described by Povey, M. J. W., and M. G. Scanlon, *J. Coll. Int. Sci.* 93 (2), 565–566 (1983), which is hereby incorporated by reference. Correlation of particle size with frequency by comparison against a scattering theory model has been described by Pinfield, V. J. et al., *Ultrasonics*, 33 (3), 243–251 (1995). This model may be improved with corrections for thermal scattering effects as described by Pinfield, V. J. and M. J. W. Povey, *J. Phys. Chem. B.* 101, 1110–1112 (1997), each of which references is incorporated by reference.

Alternatively, the relative particle size distribution can be obtained from data of amplitude and phase vs. frequency, as well as from amplitude vs. time data.

An advantage of the present invention over prior methods is that it provides a method for resolving a particle size distribution into almost any number of discrete particle sizes within the range of particles that are sensed within the selected frequency range. This is done by selecting the number of discrete frequencies within the selected frequency range at which relative particle size is correlated. It is preferred that relative particle size be determined at least at three different frequencies within the selected frequency range, more preferred that relative particle size be determined at least at 15 different frequencies within the selected frequency range and even more preferred that relative particle size be determined at least at 30 different frequencies within the selected frequency range.

The next step is to compare the magnitude vs. frequency data, or the particle size distribution, against some standard and determine the agglomerative state of the asphaltenes.

Magnitude vs. frequency data represents a distribution of relative particle sizes, rather than absolute particle sizes, and distributions of either relative or absolute particle sizes can be used as a measure of the agglomerative state of the particles in the oil. The distribution as measured in an oil is compared with a standard having a known agglomerative state and the differences between the measured distribution and the standard indicate the agglomerative state of the measured oil. For example, the baseline at 0 dB magnitude as shown in FIG. 5 could serve as the standard with comparison against the measured distribution from crude oil. The utility of such a simple standard is illustrated by the similarly flat distribution shown in FIG. 6 of crude oil treated with an agglomeration inhibitor and having no particulates. The spikey signal in FIG. 5 between about 14 MHz and 20 MHz is attributed to asphaltene particulates in the crude oil.

Figure 7:
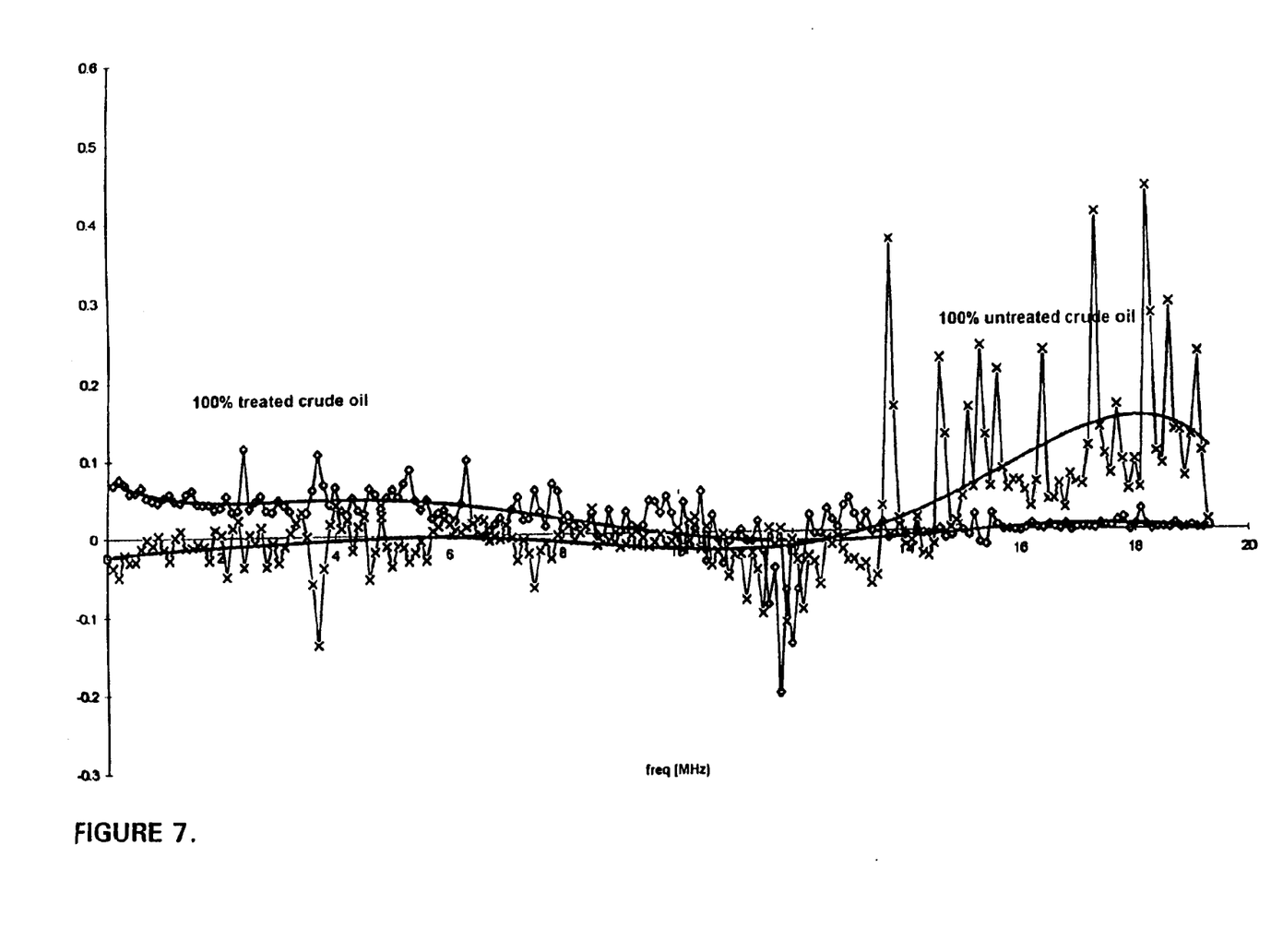
FIG. 7 is a magnitude vs. frequency plot of the data of FIG. 5 and FIG. 6 illustrating one method of comparing magnitude vs. frequency data from any oil or hydrocarbon liquid with a standard.

The use as a standard of a crude oil treated with an agglomeration inhibitor is shown in FIG. 7, where the magnitude vs. frequency distribution of the standard is superimposed over the same data for a crude oil. As above, the differences in the two signals in the frequency range between about 14 MHz and about 20 MHz indicate the presence of agglomerates in the crude.

Since the operation of the acoustic and electronic steps of the present invention take place very quickly and because no step requires waiting for a change in occur in the liquid (as in the methods disclosed by Bouts, deBoer and Anfindsen), or requires the titration or addition of any material to the liquid (as in Bouts and deBoer), the determination of agglomerative state takes place substantially instantaneously and can be advantageously applied on a real-time basis to process steams and the like. In the present case, substantially instantaneously means that the measurement can be made in less than about one second. It is understood, however, that the system applying the present method may take such measurements continually and, if desirable, can average the results of several measurements taken over any period of time desired.

Figure 9:
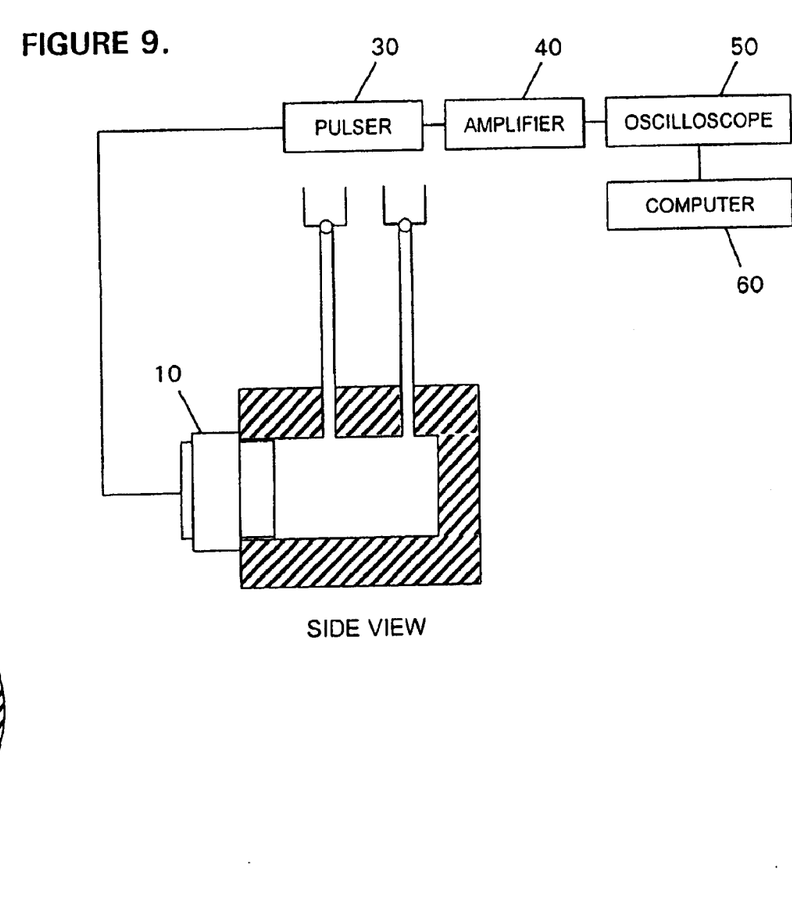
FIG. 9 is a side view of a measuring cell having one transducer adapted for bench-scale or laboratory use for practicing an embodiment of the present invention.

Use of the present invention in a device at the bench-scale, or laboratory scale, is an additional embodiment of the present invention. In a method suitable for this application, a liquid sample may be removed or conducted from the container in which the oil on which the agglomerative state of asphaltenes is to be determined. The same steps of applying acoustic energy, detecting scattered energy and resolving, deriving and determining the agglomerative state of the asphaltenes are carried out on the undiluted oil as described above, except that the applying and sensing takes place in a flow cell, or measurement cell, rather than in the process or tank. Examples of such measurement cells are shown, for example, in FIG. 9 and FIG. 10. After such measurements are complete, the undiluted, unadulterated oil sample can be returned or disposed of, as desired. An advantage of being able to return the undiluted and uncontaminated oil sample to the bulk oil is that no additional expense or effort is required for disposal of the hydrocarbon samples.

An additional embodiment of the present invention is a method for controlling the agglomeration of asphaltenes in oil. A system such as the shown in FIG. 8 can be used for such control function. The subject method involves the steps of applying a signal of acoustic energy to the oil and detecting the scattered energy over a selected frequency as described above. The detected energy is then resolved into its magnitude at selected increments within the selected frequency range. The magnitude of the detected scattered energy is related to the number of particles of a certain size and, for control purposes, it is not necessary to derive the distribution of the relative particle sizes, but only to compare the magnitude of the detected signal at one or more selected frequencies with a standard, in order to make a decision to act to control the number of particles corresponding to the particular frequency or frequencies.

As an application of the present invention is calibrated and tuned for a particular application, it may be desirable to limit the frequency range selected for detecting scattered acoustic energy to the frequency range scattered by the agglomerated asphaltene particles characteristic of the oil. Preferably, the frequency range selected for detecting scattered acoustic energy is from about 14 MHz to about 20 MHz.

The act to control the number of particles may take any number of forms. For example, the device may cause in process conditions such as flow rate, temperature, or pressure, or may cause the addition of an agglomeration inhibitor, a surfactant, or other chemical additive. Alternatively, the control act may be to divert a stream, or slow down, speed up or stop a process.

Figure 8:
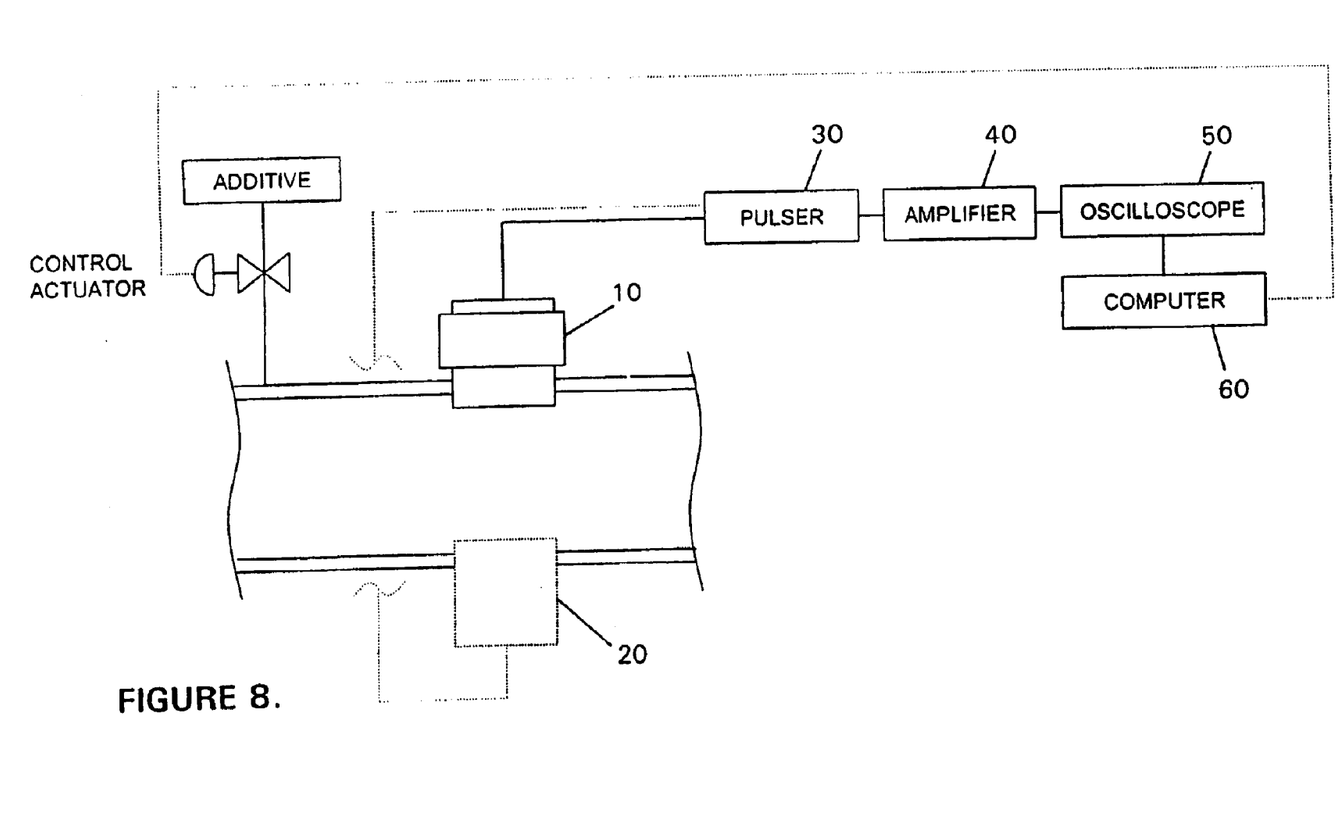
FIG. 8 is a block diagram of a system that may be used to practice an embodiment of the present invention wherein the measurement of the agglomerative state of the asphaltenes in a hydrocarbon liquid initiates an action to control agglomeration.

Use of the method for measuring the state of agglomeration in a control loop is shown in FIG. 8. The control loop can include the computer 60 and a control actuator 70, with the feedback data provided by a system applying the method for measuring the agglomerative state of the present invention.

Several particularly useful features are provided by the method of measuring the agglomerative state of asphaltenes in an oil. The measurement can be carried out on a real-time basis since there are no titrations or other additions to the oil and, thus, no waiting for changes induced by such additions. The application, detection and resolution of the acoustic signal is carried out very rapidly. Even if the detected scattered energy signal is averaged over 100 separate pulses, the relative particle size distribution can be derived and the agglomerative state of the asphaltenes determined in a time of well under one second.

The acoustic probe may be installed directly into a tank or line containing the bulk oil and the measurement may be taken on an in-line basis. No sampling is necessary. Because the test is non-diluative, if a sample is taken, it may be returned to the bulk oil, if desired, without dilution or adulteration of the oil.

Furthermore, because of the simple and resistant nature and materials of the acoustic probe, the method may be used in streams and under conditions where other methods would fail due to temperature, pressure, or corrosiveness of the oil.

Because of the features described above, the method for controlling agglomeration of asphaltenes in oil has the useful feature of being a real-time control technique. A signal from the measuring system substantially reflects the state of the oil in a process flow stream at a given time. Based on that information, actions can be taken to control the agglomeration of the asphaltenes and the results of those actions may be monitored without unacceptable time lag. A feedback control loop having a time-lag constant within normal practice is then made possible. This permits the use of conventional industrial control equipment to effect the process changes called for by the controller (in this case, the personal computer).

Industrial Application

The measuring and control systems of the present invention may be used for any in-line, in-tank, or in-process application requiring the measurement or control of the agglomerative state of asphaltenes in oil. The same measurement and control systems can also be used in a device designed for laboratory or bench-scale operation.

One potentially useful application is during production at the wellhead, or in the borehole, where changes in temperature and pressure often result in precipitation of asphaltenes from crude. This results in plugging lines and equipment and forces periodic shutdowns and maintenance to remove the asphaltene solids. Installation of a measuring and control device based on the present invention would permit addition of, for example, asphaltene precipitation inhibitors on an as-needed basis is order to minimize asphaltene agglomeration. This is an improvement over the addition of such expensive chemicals on a continuous basis because, in general, less of the inhibitor is used over time and prevention of plugging permits longer periods of operation.

The methods of the subject invention may also be applied to in-process steams, such as visbreaker streams, where hot, opaque liquids rule out most conventional particle sensors.

The following examples describes a preferred embodiment of the invention. Other embodiments within the scope of the claims herein will be apparent to one skilled in the art from consideration of the specification or practice of the invention as disclosed herein. It is intended that the specification, together with the example, be considered exemplary only, with the scope and spirit of the invention being indicated by the claims when follow the example.

EXAMPLE 1

Measurement of the state of agglomeration of asphaltenes in crude oil by a pulse-echo technique.

A system including UTEX UTP320 pulser/amplifier was used to provide a pulsed electrical signal to a 10 MHz focused ultrasonic probe. The tip of the probe was submerged in a sample of undiluted crude oil. The pulse signal used in this example had the following characteristics:

Voltage=1 kV (1,000 volts)

Duration=3 nanoseconds

Impedance=70 Ohms

Electrical power=14,285.7 watts

Efficiency=0.1

Acoustic power=1,428.57 watts

Spike frequency=1,000 Hz

On/Off Ratio=$3 \times 10^{-6}$

Mean Electrical Power=0.04286 watts

Mean Acoustic Power=0.00429 watts

The probe also acted as the sensor to detect back-scattered energy. The UTEX pulser/amplifier amplified the detected signal and transmitted it to a LeCroy Model 9320 oscilloscope. The oscilloscope carried out an analog-to-digital conversion of the signal and gated the signal to back-scatter by particles in the focal region. The gate width was approximately twice the back-scattered signal duration (i.e., 2 $\mu$s; corresponding to a focal region with a spatial extent of approximately 3 mm in oil). The oscilloscope then carried out a Fourier transform of the signal to convert it from an amplitude vs. time format to a magnitude vs. frequency format. The magnitude vs. frequency data was averaged over 200 scans prior to being exported to a personal computer for filing and further computations in an Excel® spreadsheet program. A plot of the resulting magnitude vs. frequency data is shown in FIG. 5 over a frequency range of approximately 0.1–20 MHz. A solid line showing an average value for these data points is also included on the plot.

The same type of measurement was carried out on a sample of the same oil as used above, but to which a chemical inhibitor had been added to prevent asphaltene agglomeration. The magnitude vs. frequency plot for this inhibited sample is shown in FIG. 6.

The computer compared data from the oil (as shown in FIG. 5), with the standard (as shown in FIG. 6), by superimposing one over the other as shown in FIG. 7. Alternately, the plot of FIG. 5 could simply be compared with an arbitrary baseline, such as the "0 magnitude" baseline shown in FIG. 5, or with a model, or any other standard against which the state of agglomeration of the unknown could be determined.

In FIG. 7, the trace of the asphaltene particles scattering primarily in the 14 MHz–20 MHz region can be contrasted with the lack of such scatter in the inhibited sample of the same oil. This difference represents the degree of asphaltene agglomeration in the crude oil.

In view of the above, it will be seen that the several advantages of the invention are achieved and other advantageous results attained.

As various changes could be made in the above methods and compositions without departing from the scope of the invention, it is intended that all matter contained in the above description shall be interpreted as illustrative and not in a limiting sense.

What is claimed is:

1. A method for measuring the agglomerative state of asphaltenes in oil containing asphaltenes, comprising applying to the oil a series of pulses of acoustic energy, each pulse comprising acoustic energy at multiple frequencies, thereby scattering at least part of the energy; detecting for each of a plurality of pulses in the series, the scattered acoustic energy in produce amplitude versus time data, resolving the amplitude versus time data to obtain a magnitude of the detected scattered acoustic energy at selected frequencies, averaging over the plurality of pulses the magnitude for each pulse at each selected frequency, and determining from the averaging the agglomerative state of the asphaltenes.

2. A method as set forth in claim 1 wherein the selected frequencies comprise at least three different frequencies.

3. A method as set forth in claim 1 wherein the selected frequencies comprise at least fifteen different frequencies.

4. A method as set forth in claim 1 wherein the steps are carried out without diluting the hydrocarbon liquid.

5. A method as set forth in claim 4 wherein the steps of the method are carried out substantially instantaneously.

6. A method as set forth in claim 5, wherein the detected scattered acoustic energy is back-scattered acoustic energy.

7. A method as set forth in claim 6, wherein the second acoustic energy is detected over a frequency range of from about 0.1 MHz to about 20 MHz.

8. A method as set forth in claim 7, wherein the scattered acoustic energy is detected over a frequency range of from about 0.1 MHz to about 200 MHz.

9. A method as set forth in claim 8, wherein the scattered acoustic energy is detected over a frequency range of from about 14 MHz to about 20 MHz.

10. A method as set forth in claim 1, wherein the detecting is carried out by at least one sensor which sensor is incorporated in a signal input probe.

11. A method as set forth in claim 1, wherein the detecting is carried out by at least one sensor which sensor is separate from a signal input probe.

12. A method as set forth in claim 1, wherein the resolving of the amplitude versus time data comprises gating the detected scattered acoustic energy to that part of the detected energy emanating from a local region and Fourier transforming the amplitude versus tissue data into a magnitude vs. frequency format.

13. A method as set forth in claim 1, wherein the pulses of acoustic energy are applied as a tone-burst and the step of resolving of the amplitude versus time data comprises detecting the magnitude of the scattered energy at selected frequencies.

14. A method as set forth in claim 1, wherein the averaging over the series of pulses the magnitude for each pulse at each selected frequency produces an average of the magnitude for each selected frequency, and the determining the agglomerative state of the asphaltenes is effected by comparing the that average for each selected frequency with a standard.

15. A method as set forth in claim 14, wherein the standard is a sample of known particle size.

16. A method as set forth in claim 14, wherein the standard is a model of particle size based on scattering theory.

17. A method as set forth in claim 1, wherein the oil containing asphaltenes is in a process flow stream and the signal of acoustic energy is applied to the oil in the process flow stream.

18. A method for measuring the agglomerative state of asphaltenes in an oil containing asphaltenes comprising:

a. removing a sample of the oil and without diluting the oil, b. applying to the sample a series of pulses of acoustic energy, each pulse comprising acoustic energy at a multiple frequencies, thereby scattering at least part of the energy;

c. detecting, for each of a plurality of pulses in the series, the magnitude of the scattered acoustic energy at selected frequencies to produce amplitude versus time data;

d. resolving the amplitude versus time data to obtain a magnitude of the detected scattered acoustic energy at selected incremental frequencies;

e. averaging over the plurality of pulses the magnitude for each pulse at each selected frequency;

f. deriving from the averaging a distribution of the relative size of asphaltene particles scattering acoustic energy; and g. determining the agglomerative state of the asphaltene particles.

19. A method as in claim 17, having the additional step of returning the undiluted oil sample.

20. A method for controlling the agglomeration of asphaltenes in oil which comprises applying a series of pulses of acoustic energy to the oil, each pulse comprising acoustic energy at multiple frequencies, thereby scattering at least a part of the energy, detecting for each of a plurality of pulses in the series, the scattered energy at selected frequencies to produce amplitude versus time data; resolving the amplitude versus time data to obtain a magnitude of the detected scattered energy at selected incremental frequencies, averaging over the plurality of pulses the magnitude for each pulse at each selected frequency to obtain average magnitude versus frequency data, comparing the average magnitude versus frequency data with a scandal; and acting to control the number of particles having a particle size corresponding to the selected incremental frequencies.

21. A method as set forth in claim 20, wherein the selected frequencies are limited to a frequency range of acoustic energy scattered by the agglomerated asphaltene particles characteristic of the oil.

22. A method as set forth in claim 20, wherein the scattered acoustic energy is detected over a frequency range of from about 14 MHz to about 20 MHz.

* * * * *